US007265199B2

(12) United States Patent
Grunze et al.

(10) Patent No.: US 7,265,199 B2
(45) Date of Patent: Sep. 4, 2007

(54) POLY-TRI-FLUORO-ETHOXYPOLYPHOS-PHAZENE COVERINGS AND FILMS

(75) Inventors: Michael Grunze, Neckargemünd (DE); Claudia Gries, Ulm (DE)

(73) Assignee: Celonova BioSciences Germany GmbH, Ulm (DE)

( * ) Notice: Subject to any disclaimer, the term of this patent is extended or adjusted under 35 U.S.C. 154(b) by 340 days.

(21) Appl. No.: 10/257,928

(22) PCT Filed: Apr. 10, 2001

(86) PCT No.: PCT/DE01/01398

§ 371 (c)(1),
(2), (4) Date: Jan. 23, 2003

(87) PCT Pub. No.: WO01/80919

PCT Pub. Date: Nov. 1, 2001

(65) Prior Publication Data

US 2004/0014936 A1  Jan. 22, 2004

Related U.S. Application Data

(60) Provisional application No. 60/196,083, filed on Apr. 11, 2000.

(30) Foreign Application Priority Data

Apr. 22, 2000 (DE) ................ 100 19 982

(51) Int. Cl.
*C08G 79/02* (2006.01)
*A61M 36/14* (2006.01)
*A61K 51/00* (2006.01)

(52) U.S. Cl. ............ 528/399; 528/398; 424/1.81; 424/1.11; 424/1.25; 424/1.29; 424/1.37; 424/1.61; 600/1; 600/3; 600/7; 600/8; 600/168

(58) Field of Classification Search ........... 528/399, 528/398; 604/265; 424/1.81, 1.11, 1.25, 424/1.29, 1.37, 1.61; 600/1, 3, 7, 8, 168
See application file for complete search history.

(56) References Cited

U.S. PATENT DOCUMENTS

| 4,311,736 A | 1/1982 | Leong |
| 4,318,947 A | 3/1982 | Joung |
| 4,341,844 A | 7/1982 | Leong |
| 4,424,395 A | 1/1984 | Strom |
| 4,451,647 A | 5/1984 | Allcock et al. |
| 4,480,642 A | 11/1984 | Stoy et al. |
| 4,579,880 A | 4/1986 | Ohashi |
| 4,592,755 A | 6/1986 | Penton et al. |
| 4,798,876 A | 1/1989 | Gould et al. |
| 4,880,622 A | 11/1989 | Allcock et al. |
| 4,883,699 A | 11/1989 | Aniuk et al. |
| 4,911,691 A | 3/1990 | Aniuk et al. |
| 4,975,280 A | 12/1990 | Schacht et al. |
| 5,238,569 A | 8/1993 | Soria et al. |
| 5,439,446 A | 8/1995 | Barry |
| 5,548,060 A | 8/1996 | Allcock et al. ............ 528/487 |
| 5,552,159 A | 9/1996 | Mueller et al. |
| 5,605,696 A | 2/1997 | Eury et al. |
| 5,634,946 A | 6/1997 | Slepian |
| 5,707,597 A | 1/1998 | Andrianov et al. |
| 5,716,981 A | 2/1998 | Hunter et al. |
| 5,788,979 A | 8/1998 | Alt et al. |
| 5,814,704 A | 9/1998 | Andrianov et al. |
| 5,873,904 A | 2/1999 | Ragheb et al. |
| 5,886,026 A | 3/1999 | Hunter et al. |
| 5,914,388 A | 6/1999 | Allcock |
| 5,980,972 A | 11/1999 | Ding |
| 5,997,301 A | 12/1999 | Linden |
| 6,007,573 A | 12/1999 | Wallace et al. |
| 6,077,916 A | 6/2000 | Laurencin |
| 6,254,634 B1 | 7/2001 | Anderson |
| 6,273,913 B1 | 8/2001 | Wright et al. |
| 6,319,984 B1 | 11/2001 | Song et al. |
| 6,346,110 B2 | 2/2002 | Wu |
| 6,432,128 B1 | 8/2002 | Wallace et al. |
| 6,485,514 B1 | 11/2002 | Wrenn, Jr. |
| 6,503,556 B2 | 1/2003 | Harish et al. |
| 6,506,411 B2 | 1/2003 | Hunter et al. |
| 6,569,195 B2 | 5/2003 | Yang et al. |

(Continued)

FOREIGN PATENT DOCUMENTS

| CA | 1 252 253 | 5/1986 |
| DE | 196 13 048 A1 | 10/1996 |
| DE | 196 13 048 C2 | 10/1996 |
| DE | 100 19 982 A | 10/2001 |
| DE | 101 00 961 A1 | 8/2002 |

(Continued)

OTHER PUBLICATIONS

Grunze et al, 32P-labeled polyphosphazenes, Apr. 1999, Chem Abstract 130: 272061.*
**Allcock, "Polyphosphazenes", Inorganic Polymers, 1992, pp. 61-139, XP000866367, pp. 95-117.
A. Welle et al. Blood Compatibility of Poly[bis(trifluoroethoxy)phosphazene], Institute of Applied Physical Chemistry, JAMP, vol. 4, 6-10 (2000), University of Heidelberg, Germany.
A. Welle et al., "Polyphosphazenes as Antithrombotic Coatings for Prosthetic Heart Valves," Presented at 19 Annual Meeting of the Adhesion Society, Myrtle Beach, SC, 4 pages (Feb.1996).

(Continued)

*Primary Examiner*—Duc Truong
(74) *Attorney, Agent, or Firm*—Flaster/Greenberg P.C.

(57) ABSTRACT

The present invention relates to an anti-thrombogenic, physically well-tolerated polymer and its use for manufacturing sheaths and films as a component of therapeutic devices for preventing excessive cell proliferation. Furthermore, it relates to films made from the polymer as well as wrappings for medical devices such as stents. It also relates to medical devices that are enclosed by a film or wrapping according to the invention.

17 Claims, No Drawings

U.S. PATENT DOCUMENTS

| | | | |
|---|---|---|---|
| 6,652,575 | B2 | 11/2003 | Wang |
| 6,669,719 | B2 | 12/2003 | Wallace et al. |
| 2001/0014717 | A1 | 8/2001 | Hossainy et al. |
| 2001/0029351 | A1 | 10/2001 | Faletico et al. |
| 2002/0005206 | A1 | 1/2002 | Faletico et al. |
| 2002/0094440 | A1 | 7/2002 | Llanos et al. |
| 2002/0111590 | A1 | 8/2002 | Davila et al. |
| 2002/0119202 | A1 | 8/2002 | Hunter et al. |
| 2002/0133183 | A1 | 9/2002 | Lentz et al. |
| 2002/0165608 | A1 | 11/2002 | Llanos et al. |
| 2003/0004568 | A1 | 1/2003 | Ken et al. |
| 2003/0060877 | A1 | 3/2003 | Falotico et al. |
| 2003/0065345 | A1 | 4/2003 | Weadock |
| 2003/0065377 | A1 | 4/2003 | Davila et al. |
| 2003/0153983 | A1 | 8/2003 | Miller et al. |
| 2003/0153985 | A1 | 8/2003 | Lee |

FOREIGN PATENT DOCUMENTS

| | | |
|---|---|---|
| EP | 0 150 699 A2 | 8/1985 |
| EP | 0 286 709 A1 | 10/1988 |
| EP | 0 706 376 B1 | 6/1997 |
| EP | 0 804 909 A2 | 11/1997 |
| EP | 0 970 711 B1 | 1/2000 |
| EP | 1 112 094 B1 | 7/2001 |
| EP | 1 179 353 A1 | 2/2002 |
| JP | 58-079915 A | 5/1983 |
| WO | 93/21858 A1 | 11/1993 |
| WO | 95/02628 A1 | 1/1995 |
| WO | 95/28966 A1 | 11/1995 |
| WO | 96/00103 A1 | 1/1996 |
| WO | 96/04015 A1 | 2/1996 |
| WO | 96/25176 A1 | 8/1996 |
| WO | 96/25897 A2 | 8/1996 |
| WO | 96/29059 A1 | 9/1996 |
| WO | 98/43618 A2 | 10/1998 |
| WO | 98/52605 A1 | 11/1998 |
| WO | 88/09664 A1 | 12/1998 |
| WO | 98/56312 A1 | 12/1998 |
| WO | 99/09088 A | 2/1999 |
| WO | 99/16416 A2 | 4/1999 |
| WO | 99/16477 A2 | 4/1999 |
| WO | WO99/16477 A2 | 4/1999 |
| WO | 99/42147 A1 | 8/1999 |
| WO | 99/52356 A1 | 10/1999 |
| WO | 00/32238 | 6/2000 |
| WO | 00/61204 A1 | 10/2000 |
| WO | 01/87372 A1 | 4/2001 |
| WO | 01/36008 A3 | 5/2001 |
| WO | 01/45763 A1 | 6/2001 |
| WO | 01/49340 A1 | 7/2001 |
| WO | 01/70296 A1 | 9/2001 |
| WO | WO 01/70296 A1 | 9/2001 |
| WO | 01/87368 A1 | 11/2001 |
| WO | 02/24247 A1 | 3/2002 |
| WO | 2004/011055 A2 | 2/2004 |

OTHER PUBLICATIONS

C. T. Laurencin et al., "Use of polyphosphazenes for skeletal tissue regeneration," J. Biomedical Materials Research, vol. 27, No. 7, pp. 963-973 (1993), John Wiley & Sons, Inc., USA.

F. Veronese et al., "Polyphosphazene Membranes and Microspheres in Periodontal Diseases and Implant Surgery," Biomaterials, vol. 20, 91-98 (1999), Elsevier, USA.

G. Lopez et al., "Glow Discharge Plasma Deposition of Tetraethylene Glycol Dimethyl Ether for Fouling-Resistant Biomaterial Surfaces," J. of Biomedical Materials Research, vol. 26, 415-439 (1992), John Wiley & Sons, Inc., USA.

H. Allcock et al., "Antibacterial activity and mutagenicity studies of water-soluble phosphazene high polymers," Biomaterials, vol. 13, No. 2, pp. 847-962 (1992), Butterworth-Heinemann Ltd., USA.

H. Allcock, "Polyphosphazenes," Inorganic Ploymers, pp. 61-139 (1992).

I. De Scheerder et al., "Angiopeptin Loaded Stents Inhibit the Neointimal Reaction Induced by Ploymer Coated Stents Implanted in Porcine Coronary Arteries," Abstract 772-6, pp. 286A, JACC (Feb. 1995). (Abstract).

M. kajiwara, "The Study of the Cultivation of Chinese Hamster Ovary and Bows Cell Lines, " Phosphorus, Sulfur, and Silicon, vol. 76, pp. 163-166 (1993), Gordon and Breach Science Publishers S.A., USA.

P. Kingshott, "Surfaces that Resist Bioadhesion," Current Opinion in Solid State and Materials Science, vol. 4, 403-412 (1999), Pergamon.

Ph. Potin & R. DeJaeger, "Review: Polyphosphazenes: Synthesis, Structures, Properties, Applications," European Polymer Journal, vol. 27, 341-348 (991), Pergamon Press, Great Britain.

R. De Jaeger & M. Gleria, "Poly(organophosphazene)s and Related Compounds: Synthesis, Properties and Applications," Prog. Polym. Sci., vol. 23, 179-276 (1998), Pergamon Press, Great Britain.

R. Waksman, "Vascular Brachytherapy: Applications in the Era of Drug-Eluting Stents," Reviews in Cardiovascular Medicine, vol. 3, S23-S30 (2002), MedReviews, LLC, USA.

R.R. McCaffrey et al., "Synthesis, Casting, and Diffusion Testing of Poly[bis(tri-fluoroethoxy)phosphazene] Membranes," J. of Membrane Science, vol. 28, 47-67 (1986), Elsevier Science Publishers B.V., Netherlands.

S. Cohen et al., "Design of Synthetic Polymeric Structures for Cell Transplantation and Tissue Engineering," Clinical Materials, vol. 13, 3-10 (1993), Elsevier Science Publishers Ltd, England.

S. Ibim et al., "Controlled Macromolecule Release from Poly(phosphazene) Matrices," J. of Controlled Release, vol. 40, 31-39 (Jun. 1996), Elsevier Science B.V. (Abstract).

S. Vinogradova et al., "Open-chain Poly(organophosphazenes). Synthesis and Properties," Russian Chemical Reviews, vol. 67, 515-534 (1998), Russian Academy of Sciences and Turpion Ltd.

V. Korsak et al., "On the Effect of Water on the Polymerization of Hexachlorocyclotriphosphazenes," Acta Polymerica, vol. 30, No. 5, 245-248 (1979).

Y. Lemmouchi et al., "Biodegradable Polyphosphazenes for Drug Delievery," Macromolecular Symposia, vol. 123, 103-112 (Sep. 1997) Wiley VCH, Weinheim, Germany.

* cited by examiner

POLY-TRI-FLUORO-ETHOXYPOLYPHOSPHAZENE COVERINGS AND FILMS

CROSS-REFERENCE TO RELATED APPLICATIONS

This application claims the benefit under 35 U.S.C. § 119(e) of U.S. Provisional Application Ser. No. 60/196,083, filed Apr. 11, 2000, the disclosure of which is hereby incorporated by reference in its entirety.

The present invention relates to an anti-thrombogenic, physically well-tolerated polymer and its use for manufacturing sheaths and films as a component of therapeutic devices for preventing excessive cell proliferation. Furthermore, it relates to films made from the polymer, as well as wrappings for medical devices, such as stents. It also relates to medical devices that are enclosed by a film or wrapping according to the invention.

The biggest complications caused by artificial implants are the increasing platelet deposits on the exogenous surface. In addition, the behavior toward bacteria, macrophages and proteins deposited on the surfaces of the implant plays a central role, since these deposits contribute significantly to inflammation and other problems as the implant grows in.

One of the problems that can potentially occur is increased cell proliferation and inflammation of injured tissue that comes into contact with the artificial implant. In addition to the already known problems of increased thrombogenesis, restenosis (i.e., the re-constriction of blood vessels in an area dilated by angioplasty, often the stent area) is encountered in vascular implants, e.g., so-called stents. Among other things, these complications may stem from the activation of the coagulation and immune system by the implanted foreign body, and from damage done to the vascular wall while implanting the stent during an angioplasty. The result is so-called restenosis (re-occlusion of blood vessels), and possible inflammations in the treated area, which necessitate immediate drug therapy, and frequently surgical treatment as well.

One way in which an attempt is made to prevent these complications caused by an increased cell proliferation in the stent area, involves the use of sheathed, so-called covered stents. A wide range of materials and sheathed stents used for manufacturing such wrappings have become known and been investigated in prior art. For example, an expandable wrapping made from e-PTFE is used for this purpose in WO 9856312. Other materials for this application are cited in EP 0810845, and, for example, mention polymers cited in U.S. Pat. No. 4,883,699 and U.S. Pat. No. 4,911,691. Other polymers named for the specified purpose include hydrolyzed polyacrylonitrile (U.S. Pat. No. 4,480,642), hydrophilic polyethers (U.S. Pat. No. 4,798,876) and polyurethane-di-acrylate (U.S. Pat. No. 4,424,395). Also known are different hydrogels that can be used for this purpose. The group of potentially applicable materials can also be supplemented with polyvinyl pyrrolidone (PVP) polymers, polyvinyl alcohols (PVA), p(polyethylene oxide) polymers (PEO) and poly hydroxyethyl methacrylate p(HEMA). Furthermore, publications mention the use of a group of standard materials like polyurethane, polyethylene and polypropylene as possible materials. Also known are mixtures of these materials with each other. A group of additional materials is also known from EP 0804909.

The properties of these compounds are variable, and it may be assumed that each of these materials exhibits special properties for specific applications. For example, PVA is readily soluble in liquids. Other materials have good blood tolerance. Still other materials are highly extensible. However, all materials unfortunately exhibit shortcomings in certain areas. PVA, for example, does not possess an especially good blood tolerance. e-PTFE has very good extensibility, for example, and also good blood tolerance, but this material is extremely difficult to work with, and manufacturing such wrappings requires a series of processing steps (WO 96/00103). With other materials, elastic properties can only be achieved by adding softeners, which lower tolerance in the blood and body, and also burden the patient owing to the elimination of the "softeners".

Among other things, this means that due to the inadequate properties of existing materials during postoperative treatment after an angioplasty, patients must currently be given anticoagulants (vitamin K antagonists). Determining the dosages of the latter is problematical, however.

This also means that the restenosis rate lies at approx. 30–50% within 6 months of an angioplasty for commercially available stents.

This rate should be lowered through the use of sheathed stents, by preventing cellular tissue from growing in the vascular space. However, this technology comes up against limiting factors determined above all by the materials, their physicochemical properties, and the surface quality of these materials.

The polymeric compound poly [bis(trifluoroethoxy) phosphazene] exhibits a good antithrombogenic effect as a bulk material (cf. Tur, *Untersuchungen zur Thrombenresistenz von Poly[bis(trifluoroethozy)phosphazen]* and Hollemann-Wiberg "Stickstoffverbindungen des Phosphors" *Lehrbuch der anorganischen Chemie* 666–669, 91st–100th Edition, Walter de Gruyter Verlag 1985 also Tur, Vinogradova, et al., "Entwicklungstendenzen bei polymeranalogen Umsetzungen von Polyphosphazene," *Acta Polymerica* 39: 424–429, (8)1988). Moreover, polyphosphazene was used in Patent Specification DE 196 13 048 as a coating for artificial implants.

However, this substance alone cannot limit or reduce the cell growth that leads to restenoses.

Therefore, the object of the present invention is to provide a film and a wrapping made from it for medical devices, e.g., catheters or stents of all types, which on the one hand exhibit excellent mechanical and physical tolerance properties, so as to improve the biocompatibility of sheathed medical devices, while on the other hand preventing or diminishing the aforementioned secondary injuries following treatment or implantation. In particular, supplying the specified film and the device fabricated from it is for preventing or diminishing uncontrolled cellular growth, e.g., which leads to restenoses after stent implantation. Additionally to be achieved is a decrease in inflammatory reactions, which are a common response to the introduction of a foreign material into the body, and require the administration of antibiotics.

This object is achieved by supplying a film, as well as a wrapping fabricated from it, and a stent covered by this wrapping, wherein a polymer having the following general formula (1) is used as the material for the specified films and wrappings,

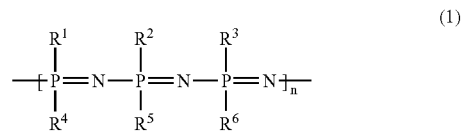

(1)

where n stands for 2 to ∞, $R^1$ to $R^6$ are either the same or different, and represent an alkoxy, alkylsulfonyl, dialkyl amino, or an aryloxy group, or a heterocyclic alkyl or heteroaryl group with nitrogen as the heteroatom.

The degree of polymerization of polymers according to formula (1) used to manufacture the film according to the invention and wrapping fabricated from it is to range from 2 to ∞. However, the degree of polymerization preferably ranges from 20 to 200,000 and more preferably from 40 to 10,000,000.

Furthermore, the polymer used for manufacturing purposes is to satisfy the following requirements:

At least one of the groups $R^1$ to $R^6$ in the polymer is preferably an alkoxy group substituted with at least one fluorine atom.

The alkyl group in the alkoxy, alkylsulfonyl and dialkyl amino groups include straight or branched chain alkyl groups with 1 to 20 carbon atoms, wherein the alkyl groups may be substituted with at least one halogen atom, such as a fluorine atom.

Examples of alkoxy groups include methoxy, ethoxy, propoxy and butoxy groups, which preferably can be substituted with at least one fluorine atom. Particularly preferred is the 2,2,2-trifluoroethoxy group. Examples of alkylsulfonyl groups are methyl, ethyl, propyl and butylsulfonyl groups. Examples of dialkyl amino groups are the dimethyl, diethyl, dipropyl, and dibutylamino groups.

The aryl group in the aryloxy group is, for example, a compound with one or more aromatic ring systems, wherein the aryl group can be substituted with at least one of the previously defined alkyl groups, for example. Examples of aryloxy groups are phenoxy and naphthoxy groups and derivatives thereof.

The heterocyclic alkyl group is for example a 3 or 7 membered ring system wherein at least one ring atom is a nitrogen atom. The heterocyclic alkyl group can, for example, be substituted by at least one of the previously defined alkyl groups. Examples of heterocyclic alkyl groups include piperidinyl, piperazinyl, pyrrolidinyl and morpholinyl groups and derivatives thereof. The heteroaryl group can be a compound with one or more aromatic ring systems, wherein at least one ring atom is a nitrogen atom. The heteroaryl group can be substituted with at least one of the previously defined alkyl groups, for example. Examples of heteroaryl groups include pyrrolyl, pyridinyl, pyridinoyl, isoquinolinyl, and quinolinyl groups and derivatives thereof.

In a preferred embodiment of the present invention, the film according to the invention and the wrapping fabricated from it using the polymer, consist of poly[bis(trifluoroethoxy)phosphazene] marked with $^{32}P$, $^{33}P$, or As or Sb isotopes.

The present invention also relates to the use of the film according to the invention and the sheath fabricated from it for the manufacture of a therapeutic device enveloped with this film for preventing excessive cell proliferation. Moreover, the film according to the invention and the sheath fabricated from it can be a constituent of other therapeutic devices, such as artificial implants, plaster or tape, artificial blood vessels, stents, catheters, ureters, or other implants without direct contact with the blood.

The film according to the invention and the sheath fabricated from it can be used in conjunction with a coating or without any special pretreatment of the implant. Further, not only can the sheathed stents according to the invention be used in arterial vessels, but also in venous vessels, in the gastrointestinal tract, in the esophagus or trachea, or the urinary tracts.

Further, the present invention supplies a therapeutic device having a sheath made out of the polymer according to formula (1).

In a preferred embodiment of the present invention, an artificial implant material is supplied, which comprises an implant material as substrate and a biocompatible coating that consists of the polymer with the aforementioned general formula (1) and is applied at least partially on the substrate surface.

The biocompatible coating of the artificial implant according to the invention has, for example, a thickness of about 1 nm to about 100 μm, preferably up to about 10 μm, and especially preferred up to about 1 μm.

The implant material used as the substrate according to the invention has no special limitation, and can be any implant material, such as plastics, metals, metal alloys and ceramics. In particular, the implant material can be a ceramic or a metallic stent material.

In another embodiment of the artificial implant according to the invention, a layer containing an adhesion promoter is incorporated between the surface of the substrate and the biocompatible coating consisting of the polyphosphazene derivative.

The adhesion promoter or spacer preferably contains a polar end-group. Examples include hydroxy, carboxy, carboxyl, amino, or nitro groups. However, use can also be made of type O-ED end groups, wherein O-ED stands for an alkoxy, alkylsulfonyl, dialkyl amino, or aryloxy group, or a heterocycloalkyl or heteroaryl group with nitrogen as the heteroatom, and can be varyingly substituted, e.g., by halogen atoms, especially fluorine.

In particular, the adhesion promoter can be an organosilicon compound, preferably an amino-terminated silane, or based on aminosilane, amino-terminated alkenes, nitro-terminated alkenes, and silanes, or an alkylphosphonic acid. Aminopropyl trimethoxy silane is especially preferred.

In particular, the adhesion promoter improves adhesion of the coating to the surface of the device or implant material by coupling the adhesion promoter to the surface of the implant material, e.g., via ionic and/or covalent bonds, and by further coupling the adhesion promoter to reactive components, especially to described general formula (1) polymers of the coating, for example via ionic and/or covalent bonds.

In general, the film according to the invention and the wrapping are manufactured as follows:

A solution containing at least one compound with general formula (1) in a concentration of 0.1% to 99%, in a solvent, wherein this solvent is organic and polar. For example, ethyl acetate, acetone, THF, toluene, or xylenes can be used here. Mixtures of these solvents can also be used, or supplemented with other solvents. This solution is applied to a substrate that exhibits little or no adhesion to the polymer, e.g., glass, silicon, various ceramics or other appropriate materials, like polymers (PDMS, Teflon, PMMA, polycarbonate or silicones). The surfaces of the specified substrates surfaces can also be chemically modified, e.g., by introducing specific functional groups (—$NH_2$, —OH, —COOH, —COH, —COOMe, —$CF_3$, etc.).

Although the solvent can be evaporated without any additional measures, the solvent vapor concentration over the substrate is optimally set in a controlled manner, as is also the pressure and the temperature. At the start of the initial drying phase, the atmosphere over the coated substrate is to be saturated with solvent vapor, and the solvent vapor concentration is then slowly reduced over a period of several hours. The temperature can vary from −30° C. up to +90° C. The pressure during the initial drying phase can range from normal pressure to water jet pressure (20 Torr). After the initial drying phase, the coated substrate is dried further for a fixed time in an oil-pump vacuum (0.1 Torr).

The polymer of compound 1 dried on the substrate can then be peeled off the substrate as a film. Depending on the concentration of the polymer solution of compound 1 and the particular conditions during the first drying phase, this yields films of varying layer thickness ranging from 0.1 μm to 300 μm or more, preferably ranging from 0.5 μm to 30 μm, and especially preferred measuring around 5 μm.

In a particular embodiment, the films or wrapping can also be microstructured according to the specified steps.

In this case, the substrate onto which the solution of compound (1) is applied is microstructured. The structure of the substrate is carried over 1:1 to the structure of the film of the used polymer. One is not limited by the structural size of the substrate. Therefore, structures on the order of nanometers, microns or even larger or smaller can be manufactured. In addition, the embodiment used in structuring is subject to no limitation. This makes it possible to manufacture and use all structures that can be generated via photolithography, electron beams or ion beams, or lasers or other techniques. In particular, structures having an especially favorable flow profile can be generated. These include lotus structures or structures resembling the "shark skin" known from aircraft construction. The special advantage to these structures and their use in manufacturing films and wrappings lies in the reduction of so-called contact activation of the coagulation system.

The polymer of compound 1 dried on the substrate can then be peeled off the substrate as a structured film and further processed. Depending on the concentration of the polymer solution of compound 1 and the discussed conditions during the first drying phase, this yields films of varying layer thickness ranging from 0.1 μm to 300 μm or more, preferably ranging from 0.5 μm to 30 μm, and especially preferred measuring around 5 μm.

The film microstructure can also be obtained by directly "writing" on the already present film itself by means of laser, electron, or X-rays, or through "melt structuring", wherein a thin wire is brought to the melting point of the polymer, and then melts the desired structure into the film via direct contact.

Special advantages can be achieved by means of this structuring by impressing structures in the film that impart a particularly favorable flow behavior to liquids (e.g., shark skin or lotus effect). This makes it possible to further diminish the contact activation of blood and further ameliorate the risk of thrombocyte aggregation in the case of sheathed stents. However, this type of structuring is not limited to the manufacture of sheathed stents, but can also be used to fabricate catheters or tubing in continuous flow systems, such as support systems, angioplasty catheters, ureters, etc. Similarly, the inner parts of dialysis devices can be shaped in this way, for example, thereby reducing the need for Heparin.

The wrapping is manufactured according to the following procedure.

The film of compound 1 obtained according to the above process is tailored to the size of the stents (+2 mm). The stents are then placed in a mount and wound with the film of compound 1 in such a way that the film extends a uniform 1 mm over both ends. The film wound around the stents can be one or more layers thick. The ends of the wrapping produced in this way along with the individual layers of the film are then heat-sealed on all sides, inside and outside, "welded" in the hot solvent vapor. To this end, the solvent is heated to a temperature of 40–120° C., optimally to 80° C. or a higher temperature. The solvent vapor rises and flows out of a very fine tube provided with one or more nozzles. Depending on its length and material, this tube can be heated and is held at a specific angle to the rising solvent vapor, so that the solvent vapor that partially condenses in the nozzle tube can drain back into the vessel without jamming the nozzles or impeding the outflow of rising solvent vapor.

The implants also obtained using the film and sheathing according to the invention surprisingly retain the excellent mechanical properties of the device and implant material. This not only improves the biocompatibility of such artificial implants, but also reduces uncontrolled cell growth, which, for example, leads to restenoses after a stent implant, by preventing cell growth in the vascular space. Moreover, using a microstructured film according to the invention makes it possible to virtually forestall the contact activation of the coagulation system.

The invention claimed is:

1. A method of manufacturing a polymer film comprising:
dissolving in solvent a biocompatible polymer with the following general formula (I),

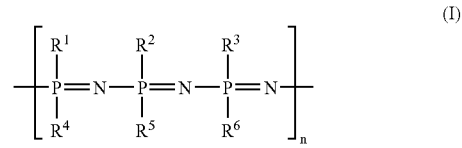

wherein n is 2 to ∞, and wherein $R^1$ to $R^6$ are either the same or different, and represent an alkoxy, alkylsulfonyl, dialkyl amino or aryloxy group, or a heterocyclic alkyl or heteroaryl group with nitrogen as the heteroatom, applying the polymer dissolved in the solvent to a substrate,
evaporating the solvent to form the polymer film,
removing the film from the substrate, wherein the film is configured for use as a wrapping or sheath and
placing the wrapping or sheath around a medical device.

2. The method according to claim 1, wherein the polymer film is antithrombogenic.

3. The method according to claim 1, wherein the device is selected from the group consisting of artificial implants, plasters, tapes, artificial blood vessels, stents, catheters, and ureters.

4. A therapeutic device comprising an implant or device substrate enveloped by a wrapping or a sheath, wherein the wrapping or sheath comprises the polymer of formula (I),

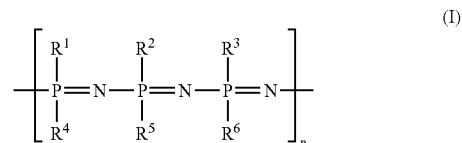

wherein n is 2 to ∞, and wherein $R^1$ to $R^6$ are either the same or different, and represent an alkoxy, alkylsulfonyl, dialkyl amino or aryloxy group, or a heterocyclic alkyl or heteroaryl group with nitrogen as the heteroatom.

5. The device according to claim 4, wherein the device is a sheathed stent.

6. The device according to claim 4, wherein the device is an artificial implant.

7. The device according to claim 6, wherein the artificial implant comprises a substrate comprising an implant material having a biocompatible coating thereon, the biocompatible coating is at least partially applied to a surface of the substrate, and the coating comprises the polymer of formula (I).

8. The device according to claim 7, wherein a layer containing an adhesion promoter is situated between the surface of the substrate and the biocompatible coating.

9. The device according to claim 8, wherein the adhesion promoter contains a polar end group, and wherein the polar end group is an organosilicon compound.

10. The device according to claim 9, wherein the organosilicon compound is aminopropyltrimethoxysilane.

11. The device according to claim 4, wherein the device is a sheathed implant substrate, the implant comprises a substrate comprising an implant material and having a biocompatible coating, the biocompatible coating is at least partially applied to the surface of the substrate, and the implant material comprises the polymer according to formula (I).

12. A microstructured polymer film of the formula (I),

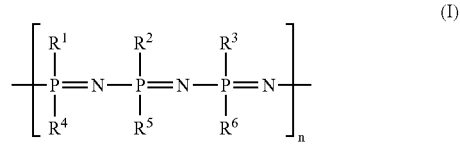

wherein n is 2 to ∞, and wherein $R^1$ to $R^6$ are either the same or different, and represent an alkoxy, alkylsulfonyl, dialkyl amino or aryloxy group, or a heterocyclic alkyl or heteroaryl group with nitrogen as the heteroatom.

13. The microstructured film according to claim 12, wherein the structures are uniform, and have a favorable flow profile.

14. The film according to claim 12, wherein the structures of the film are generated directly by means of laser, electron, or x-rays, or with a heated wire on the film.

15. The method according to claim 1, wherein the substrate is a microstructured stamp.

16. The microstructured polymer according to claim 12, wherein the film is an antithrombogenic wrapping or a sheathed substrate.

17. The method according to claim 1, wherein the medical device has a coating applied to a surface of the device according to formula (I).

* * * * *